(12) United States Patent
Ritter

(10) Patent No.: US 11,957,865 B2
(45) Date of Patent: Apr. 16, 2024

(54) DEVICE FOR CLAMPING AND HOLDING MEDICAL HOSE LINES

(71) Applicant: B. Braun Avitum AG, Melsungen (DE)

(72) Inventor: Kai-Uwe Ritter, Bethlehem, PA (US)

(73) Assignee: Braun Avitum AG, Melsungen (DE)

( * ) Notice: Subject to any disclaimer, the term of this patent is extended or adjusted under 35 U.S.C. 154(b) by 0 days.

(21) Appl. No.: 17/863,375

(22) Filed: Jul. 12, 2022

(65) Prior Publication Data

US 2023/0027003 A1 Jan. 26, 2023

(51) Int. Cl.
*A61M 39/28* (2006.01)
*F16K 7/06* (2006.01)

(52) U.S. Cl.
CPC ........... *A61M 39/284* (2013.01); *F16K 7/063* (2013.01)

(58) Field of Classification Search
CPC .............. A61M 5/1418; A61M 39/284; A61M 16/0488; A61M 16/0493; A61M 39/28; A61M 25/02; A61M 2025/0024; A61M 2025/0253; A61M 2025/026; F16K 7/02; F16K 7/04; F16K 7/06; F16K 7/063; F16K 7/066
USPC .................................................. 251/9, 10, 4
See application file for complete search history.

(56) References Cited

U.S. PATENT DOCUMENTS

| 2,603,237 | A | * | 7/1952 | Hyning | ............... | A61M 3/0266 24/339 |
| 4,406,042 | A | | 9/1983 | McPhee | | |
| 4,688,961 | A | | 8/1987 | Shioda et al. | | |
| 5,188,609 | A | * | 2/1993 | Bayless | ................... | F16L 3/137 604/174 |
| 5,203,056 | A | | 4/1993 | Funk et al. | | |
| 5,507,460 | A | * | 4/1996 | Schneider | ............... | F16L 3/223 24/601.2 |
| 5,709,665 | A | * | 1/1998 | Vergano | ............... | A61G 7/0503 604/179 |
| 6,113,062 | A | * | 9/2000 | Schnell | ............... | A61M 39/284 251/10 |

(Continued)

FOREIGN PATENT DOCUMENTS

| CN | 103672174 A | 3/2014 |
| CN | 104491972 A | 4/2015 |

(Continued)

*Primary Examiner* — Kevin F Murphy
*Assistant Examiner* — Jonathan J Waddy
(74) *Attorney, Agent, or Firm* — Christopher A. Rothe; Culhane Meadows PLLC

(57) ABSTRACT

A device for clamping and holding medical hose lines includes a hose clamp with two clamping legs on opposite sides of a passage. The passage is configured to receive a first hose portion. The clamping legs are movable between a clamping position, in which the clamping legs constrict the passage and clamp the first hose portion, and a release position in which the constriction is eliminated. The device also includes a holding clip connected to the hose clamp. The holding clip has two arms arranged opposite one another bordering a recess. The recess is configured to receive at least one second hose portion to be held between the arms. The arms are movable relative to one another between an open position, in which the arms expose a slot opening radially into the recess, and a holding position in which the slot is closed or at least constricted.

15 Claims, 4 Drawing Sheets

(56) References Cited

U.S. PATENT DOCUMENTS

| | | |
|---|---|---|
| 6,804,866 B2 | 10/2004 | Lemke et al. |
| 6,942,532 B2 | 9/2005 | Snyder |
| 7,055,784 B2 | 6/2006 | Stigler |
| 7,241,071 B2 | 7/2007 | Carraher et al. |
| 8,177,736 B2 | 5/2012 | Kopperschmidt |
| 8,333,745 B2 | 12/2012 | Tully et al. |
| 8,430,128 B2 | 4/2013 | Balteau |
| 9,903,511 B2 | 2/2018 | Vermillion |
| 10,898,639 B1* | 1/2021 | Lamb .................... A61M 5/008 |
| 2002/0083564 A1 | 7/2002 | James |
| 2007/0239121 A1* | 10/2007 | Tully .................... A61F 5/4404 |
| | | 604/326 |
| 2007/0282272 A1* | 12/2007 | Bannon ............... A61M 5/1418 |
| | | 604/174 |
| 2009/0306574 A1* | 12/2009 | Kopperschmidt .. A61M 1/3655 |
| | | 604/6.16 |
| 2010/0168682 A1 | 7/2010 | Braga et al. |
| 2010/0294271 A1 | 11/2010 | Pittaway et al. |
| 2011/0011989 A1* | 1/2011 | Samolej ................... F16L 3/24 |
| | | 248/74.3 |
| 2011/0112489 A1 | 5/2011 | Balteau |
| 2011/0288441 A1 | 11/2011 | Taguchi |
| 2012/0277682 A1* | 11/2012 | Corato .................... F16L 3/26 |
| | | 604/179 |
| 2014/0236041 A1* | 8/2014 | Gulliver ............... A61M 5/1418 |
| | | 600/549 |
| 2014/0243625 A1 | 8/2014 | Warren |
| 2015/0306305 A1* | 10/2015 | Kluttz ................. A61M 5/1418 |
| | | 248/219.4 |
| 2016/0193073 A1 | 7/2016 | Kinsey et al. |
| 2017/0328482 A1 | 11/2017 | Brugger et al. |
| 2020/0197602 A1* | 6/2020 | Corato .................... F16B 2/08 |

FOREIGN PATENT DOCUMENTS

| | | |
|---|---|---|
| CN | 204840435 U | 12/2015 |
| EP | 0517000 B1 | 10/1995 |
| FR | 2889807 A1 | 2/2007 |
| FR | 3017522 B1 | 2/2016 |
| JP | 3122020 U | 5/2006 |
| WO | 2016040232 A1 | 3/2016 |
| WO | 2021055929 A1 | 3/2021 |

* cited by examiner

DEVICE FOR CLAMPING AND HOLDING MEDICAL HOSE LINES

CROSS-REFERENCE TO RELATED APPLICATION

This application claims priority under 35 U.S.C. § 119 to German Application No. 10 2021 207 509.6, filed Jul. 14, 2021, the content of which is incorporated by reference herein in its entirety.

FIELD

The present disclosure concerns a device for clamping and holding medical hose lines.

BACKGROUND

Medical hose lines are used for widely varying therapeutic and diagnostic applications, and in principle serve for transferring bodily fluid or medical fluid.

To clamp such medical hose lines, hose clamps are known. For example, EP 0 517 000 B1 describes a hose clamp for medical purposes. The known hose clamp has a yoke-like body with a passage and two clamping legs arranged on opposite sides of the passage. The passage is configured to receive a hose portion of the medical hose line which is to be clamped between the clamping legs. The clamping legs can be moved towards one another in order to constrict the passage and hence clamp the hose portion.

In order to hold—or in the broadest sense, organize—medical hose lines, in particular the use of adhesive strips has become established practice. Often, medical hose lines are delivered or used in at least partially coiled state. This reduces the packing volume and facilitates handling. The hose windings form coils which are then usually held together by means of adhesive tape or similar.

After partial unrolling, the remaining hose coils are usually (again) bundled with adhesive tape, cable ties or similar during use of the hose line. To this end, holding elements are known. For example, US 2016/0193073 A1 discloses a holding element with several C-shaped recesses into which portions of a medical hose line to be held can be clipped.

SUMMARY

The object of the present disclosure is to provide a device of the type cited initially which allows reliable clamping and holding of medical hose lines, offers advantageous usage, and has as simple a structure as possible. Also, production should be as economic as possible.

The device according to the present disclosure comprises a hose clamp and a holding clip connected to the hose clamp. The hose clamp has two clamping legs arranged on opposite sides of a passage, wherein the passage is configured to receive a first hose portion to be clamped between the clamping legs, and wherein the clamping legs are movable relative to one another between a clamping position, in which the clamping legs are moved towards one another in order to constrict the passage and hence clamp the first hose portion, and a release position in which the constriction is eliminated. The holding clip comprises at least two holding arms which are arranged opposite one another bordering a recess, wherein the recess is configured to receive at least one second hose portion to be held between the holding arms, and wherein the holding arms are movable relative to one another between an open position, in which the holding arms are moved away from one another and expose a slot opening radially into the recess, and a holding position in which the slot is closed or at least constricted. The present disclosure is based on the knowledge that the normal use of adhesive tape or holding elements entails various disadvantages: the adhesive tape is often applied manually to the medical hose line during production. Automation is not possible or only with difficulty. This is associated with an increased production cost. During use of medical hose lines, medical personnel must remove the adhesive tape manually. This is only possible with two hands and is therefore comparatively complex and time-consuming. If the adhesive tape holds several hose coils and/or hose portions together, removal of just one single hose coil and/or single hose portion is not possible. Usually, the adhesive tape can only be removed completely, so that after complete removal, all hose coils and/or hose portions are released. Here there is a danger that a hose end of the hose line will fall to the ground, constituting a risk of contamination. After removal of the adhesive tape, often sticky residue remains on the medical hose line. This sticky residue obstructs handling and is also undesirable for hygienic reasons. After removal, the adhesive tape must be disposed of and creates waste. The same applies accordingly to known holding elements. The solution according to the present disclosure overcomes these disadvantages. To this end, the hose clamp and holding clip are connected together. During use, this counters an undesired dropping of the device to the ground: if the hose clamp is moved into the release position, and in some cases the first hose portion removed from the passage, the device may still remain fixed at the second hose portion by the holding clip. If, conversely, the holding clip is moved into the open position and the second hose portion is removed from the recess, the device may still be held at the first hose portion by the hose clamp. Also, the slot opening radially into the recess allows simple removal and reinsertion of the at least one second hose portion. The first hose portion and the second hose portion may be interconnected portions of the same medical hose line. Alternatively, the first hose portion and the second hose portion may be separate portions of separate medical hose lines. Also, it is understood that neither the first hose portion nor the second hose portion are part of the device. The two clamping legs border the passage on mutually opposing sides, for example on a top and a bottom side. In the clamping position, the two clamping legs are moved towards one another. This reduces a distance between the two clamping legs and constricts the passage. In the release position, the two clamping legs are moved away from one another. This increases the distance between the two clamping legs and eliminates the constriction of the passage. Preferably, the two clamping legs are movable relative to one another between the clamping and the release position by pivoting and/or by bending. The two clamping legs may also be described as the first clamping leg and second clamping leg. The at least two holding arms may also be designated the first holding arm and the second holding arm. Embodiments of the present disclosure provide more than two, for example three, four, five, six or more holding arms. The recess formed between the at least two holding arms has preferably a C-shaped, U-shaped and/or O-shaped basic form, or has at least one portion with such a basic form. In the holding position, the second hose portion is held in the recess by radial form fit. In the holding position, the slot is closed or at least constricted by the at least two holding arms. To this end, in the holding position, the at least two holding arms are moved towards one another starting from the open position. In the open position, the slot is opened so that the second hose portion can be inserted radially into the recess through the slot, or conversely radially removed therefrom. During use of the device, the first hose portion is oriented coaxially to a longitudinal axis of the passage. Also, the second hose portion is oriented coaxially to a longitudinal axis of the recess.

In one embodiment, the holding clip is arranged on one of the two clamping legs and the holding arms each protrude from the respective clamping leg. Insofar as the respective clamping leg is an upper one of the two clamping legs, the holding arms preferably protrude upward. Insofar as the respective clamping leg is, conversely, a lower one of the two clamping legs, the holding arms preferably protrude downward. Preferably, a main longitudinal extent direction of the respective clamping leg and main longitudinal extent directions of the holding arms are oriented transversely, preferably orthogonally to one another. This embodiment allows a particularly simple structure. This is particularly true in comparison with an embodiment in which at least one of the at least two holding arms is arranged on each of the two clamping legs. In addition, the protruding holding arms allow an easier and particularly ergonomic handling of the device.

In a further embodiment, the holding arms and the clamping legs are arranged such that a longitudinal axis of the recess and a longitudinal axis of the passage are oriented at least substantially parallel. The inventor has found that such an orientation offers advantages for a plurality of applications of the device. In further embodiments, the longitudinal axes are arranged in parallel planes transversely, preferably orthogonally, to one another.

In a further embodiment, the holding arms, at least in the open position, form a hopper-like widened inlet which, in the radial direction of the recess, opens at one end into the environment and at the other end into the slot. The hopper-like widened inlet formed between the at least two holding arms allows easier insertion of the second hose portion into the recess.

In a further embodiment, the at least two holding arms each have an S-shape and are arranged mirror-symmetrically with respect to a plane of symmetry. To put it simply, the S-shaped holding arms are arranged "back to back". Viewed from top to bottom, preferably firstly a hopper-like inlet, then the slot and below this the recess is formed between the two S-shaped holding arms. The S-shaped form of the at least two holding arms has proved particularly advantageous.

In a further embodiment, for movement between the holding position and the open position, the holding arms are each spring-elastically flexible and/or elastically preloaded in the direction of the holding position. This allows a particularly simple structure and/or avoids an undesired radial slippage of the second hose portion out of the recess. The spring-elastic flexibility of the holding arms is achieved by an elastic material and/or a bend-flexible shape of the holding arms. Preferably, the holding arms each extend in the form of a rod between a first end and a second end, and have a cross-section which is slender in comparison with the longitudinal extent, and preferably round or square. In a further embodiment, a movement of the holding arms as relatively rigid bodies between the holding position and the open position is provided, wherein for this the holding arms may be pivotably movable about a pivot axis and/or pivot axle.

In a further embodiment, the holding arms in the holding position are arranged crossed over one another and hooked together in the region of a respective end facing away from the hose clamp. The slot is completely closed in the radial direction by the crossing and engagement of the holding arms. The outer ends could also be described as the radially outer ends. Preferably, on the end face, the holding arms each have a thickening, wherein the thickening counters an undesired release of the mutually engaged holding arms. Preferably, the thickenings are formed ball-shaped.

In a further embodiment, the holding arms are arranged offset to one another by a longitudinal offset along the longitudinal axis of the recess and/or oriented with opposite longitudinal slope. The longitudinal offset and/or the opposite longitudinal slope of the holding arms allows simple production. This is particularly the case if the holding clip or the entire device is made of plastic by injection moulding. Then the longitudinal offset and/or the longitudinal slope allows simple removal from the mould and the use of simple casting moulds. Preferably, the longitudinal offset is small in relation to the other dimensions of the holding arms, so that only a narrow longitudinal gap is formed between the two holding arms. In a further embodiment, at least one of the two clamping legs has opposite leg portions arranged on both sides of the passage, wherein the leg portions are arranged offset to one another by a longitudinal offset along the longitudinal axis of the passage and/or oriented with opposite longitudinal slopes. The longitudinal offset and/or the opposite longitudinal slopes of the leg portions again allows simple production. This is particularly the case if the hose clamp or the entire device is made of plastic by injection moulding. Then the longitudinal offset and/or the longitudinal slope of the leg portions allows simple removal from the mould and the use of simple casting moulds. Preferably, the longitudinal offset is small in relation to the other dimensions of the clamping legs, so that only a narrow longitudinal gap is formed between the two leg portions.

In a further embodiment, the recess is configured to receive several second hose portions to be held and has a diameter which is many times greater than an inner width of the passage in the release position. In other words, the recess has a cross-sectional area which is many times larger than a cross-sectional area of the hose line to be held. In use of the device, thus several hose coils can be held and/or organized in the recess. For example, the recess may be configured to receive two, three, four, five, six or more hose portions. In this case, a cross-sectional area of the recess associated with the diameter amounts to a multiple of two, three, four, five, six or more times the cross-sectional area of the medical hose line. The inner width of the passage in the release position is preferably slightly smaller than the outer diameter of the medical hose line.

In a further embodiment, three holding arms are provided. Preferably, the three holding arms are arranged offset to one another in the longitudinal direction of the recess, so that with respect to the longitudinal direction, they may be described as a front, a middle and a rear holding arm. Preferably, two of the three holding arms are arranged on a common side of the recess, and the remaining third arm is arranged on an opposite side of the recess. This embodiment in particular allows the application of comparatively large holding forces in the holding position, so that the at least one second hose portion can be held in the passage particularly reliably.

In a further embodiment, for movement between the clamping and the release position, the clamping legs are each spring-elastically flexible and/or elastically preloaded in the direction of the release position. The spring-elastic flexibility of the two clamping legs may be achieved by an elastic material and/or a bend-flexible shape of the clamping legs. The elastic preload in the direction of the release position counters an undesired clamping of the first hose portion. Preferably, the clamping legs are connected together at one end, preferably integrally. In further embodiments, the clamping legs are movable as rigid bodies between the clamping and release position, and can for example be pivoted towards and away from one another about a pivot axis in the geometric or spatial-physical sense.

In a further embodiment, the clamping legs each have a latching portion on the end face, wherein the latching portions are releasably latched together in the clamping position. This prevents an undesired movement into the release position.

In a further embodiment, the hose clamp and the holding clip are integrally cohesive and form a common component. Preferably, the component is made of plastic. Preferably, it is produced by injection moulding. This embodiment allows a simple and economic production in large quantities.

In a further embodiment, the hose clamp forms an integral first component, the holding clip forms an integral second component, and the first component and second component are joined together, preferably releasably. To this end, a latching, clamping, push-fit or other connection may be formed between the first and second components. In principle, this embodiment allows a separate use of the hose clamp on one side and the holding clip on the other. Also, simplified production can be achieved. Preferably, both components are injection moulded from plastic.

In a further embodiment, the holding clip has a foot portion from which the at least two holding arms protrude, and at least one latching portion is arranged on the foot portion and is configured for latching to an outer contour of the hose clamp. The foot portion lies on one of the two clamping legs and is latched thereto by means of the latching portion. The latching portion is preferably configured in the form of a latching hook which is movable in sprung fashion.

BRIEF DESCRIPTION OF THE DRAWINGS

Further advantages and features of the present disclosure arise from the following description of preferred embodiments which are illustrated in the drawings.

DETAILED DESCRIPTION

Figure 1:
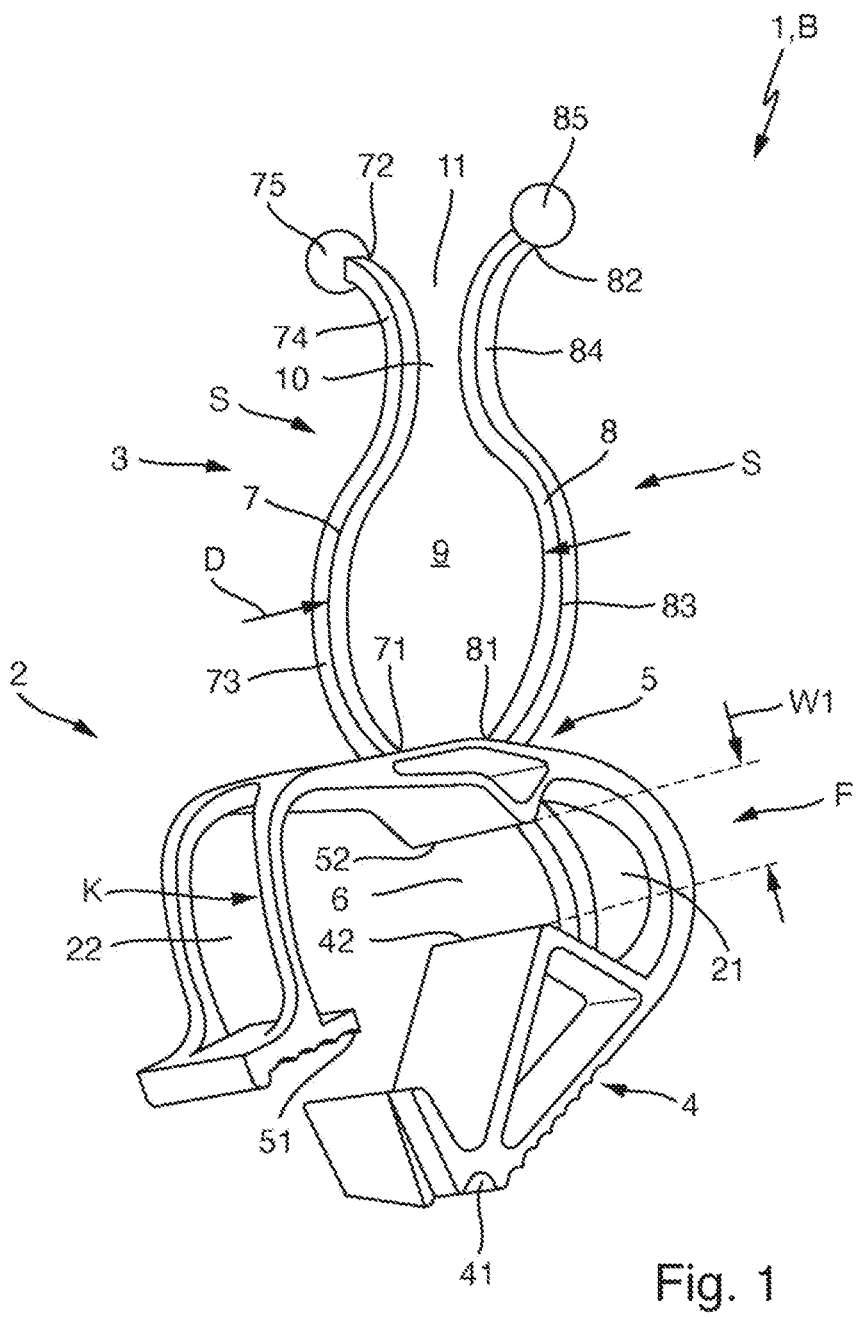
FIG. 1 shows, in a schematic perspective illustration, an embodiment of a device according to the present disclosure for clamping and holding medical hose lines.
Figure 2:
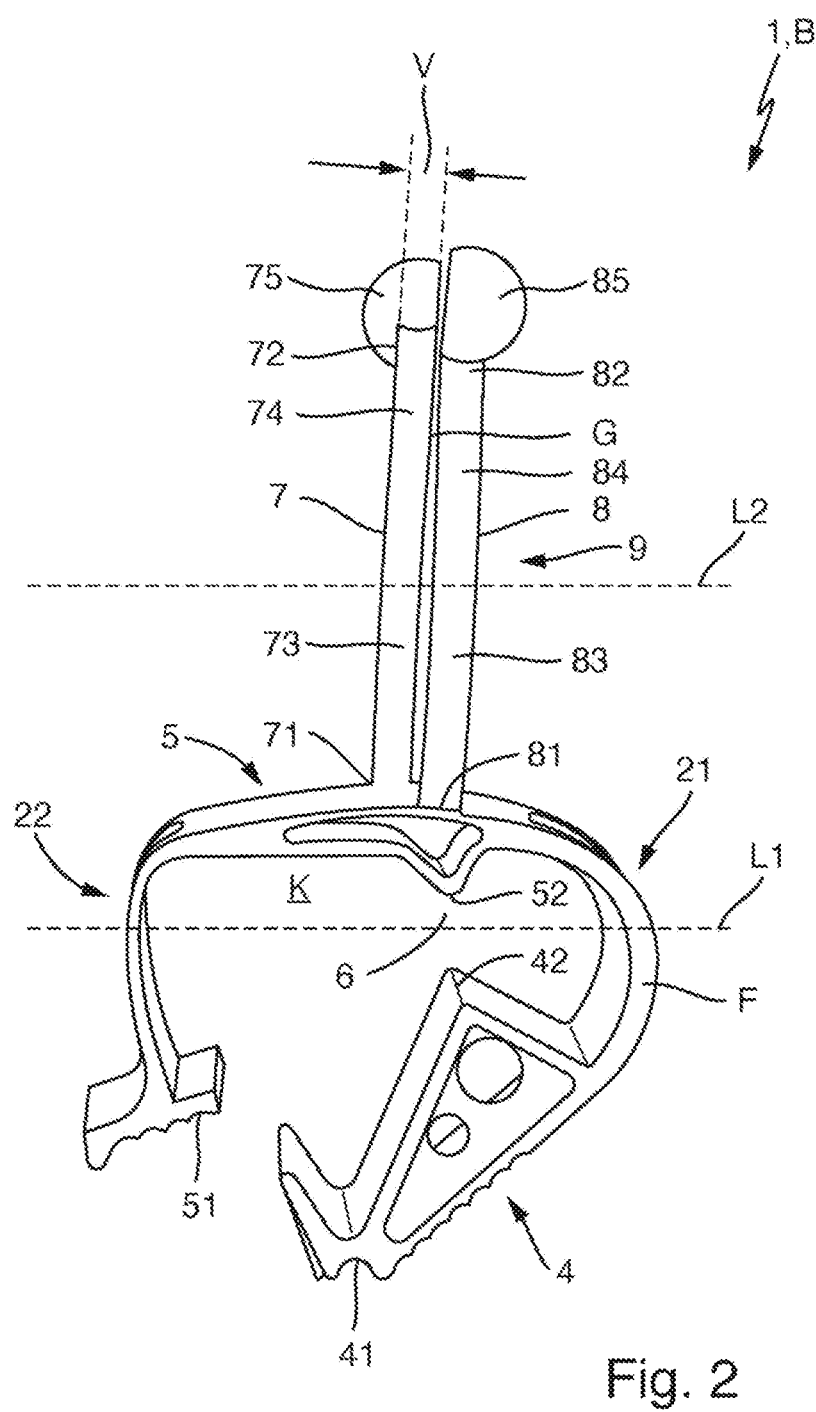
FIG. 2 shows the device from FIG. 1 in a perspective view from the side.

According to FIGS. 1 and 2, a device 1 is provided for clamping and holding medical hose lines, and comprises a hose clamp 2 and a holding clip 3 connected to the hose clamp 2. The hose clamp 2 is configured for clamping a first hose portion (not shown in detail) of the medical hose line. The holding clip 3 is configured for holding a second hose portion (not shown in detail) of the medical hose line.

The hose clamp 2 has two clamping legs 4, 5 which are arranged on opposite sides of a passage 6. The passage 6 is configured for receiving said first hose portion, wherein the first hose portion can be clamped between the clamping legs 4, 5 in a fashion to be described in more detail below. In the embodiment shown, the clamping legs 4, 5 are arranged on an underside or top side respectively of the passage 6. The clamping legs 4, 5 are also referred to below as the first clamping leg 4 and second clamping leg 5. During use of the device 1, the first hose portion extends through the passage 6 along the longitudinal axis L1 thereof, and is arranged between the first clamping leg 4 and the second clamping leg 5. For clamping and release of the first hose portion, the two clamping legs 4, 5 are movable relative to one another between a clamping position and a release position, wherein the release position is shown in FIGS. 1 and 2. Because of the relative movability of the two clamping legs 4, 5, an inner width of the passage 6 is changeable. In the release position shown (FIGS. 1, 2), the passage 6 has a first inner width W1. In the clamping position, the inner width is significantly reduced so that the passage 6 is constricted and thus the first hose portion received therein is clamped. In the release position, said constriction is however eliminated and the first hose portion released.

The holding clip 3 has at least two holding arms 7, 8. In the embodiment shown, precisely two holding arms are provided. The holding arms 7, 8 are also referred to below as the first holding arm 7 and the second holding arm 8. The holding arms 7, 8 are arranged opposite one another, bordering a recess 9. The recess 9 is configured to receive the second hose portion which is to be held between the two holding arms 7, 8. The holding arms 7, 8 are movable relative to one another between an open position and a holding position. FIGS. 1 and 2 show the open position. The holding position is not illustrated in detail in the drawings. In the open position, the holding arms 7, 8 are moved away from one another so as to expose a slot 10 opening radially into the recess 9. In said holding position, the holding arms are moved towards one another, wherein the slot 10 is closed, or at least constricted, in a manner to be described in more detail. During use of the device 1, the second hose portion to be held extends through the recess 9 along a longitudinal axis L2 thereof. For insertion into the recess 9, the second hose portion can be brought into the recess 9 through the slot 10 in the radial direction of the recess 9, wherein for this the two holding arms 7, 8 must assume the open position. In order to hold the second hose portion in the recess, the two holding arms 7, 8 are moved towards each other in a fashion to be described in more detail, and the slot 10 is closed.

In the clamping position, the first hose portion is elastically deformed so that no fluid flow is possible. In other words, the first hose portion is clamped off. However, the second hose portion is merely held in the holding position and thus secured against release from the holding clip. Here, there is no elastic deformation in the sense of clamping.

In the embodiment shown, the holding clip 3 is arranged on one of the two clamping legs 4, 5, here the second clamping leg 5. The two holding arms 7, 8 each protrude outwardly, approximately at right angles, from the second clamping leg 5. In an embodiment which is not shown, the holding clip is instead arranged on the first clamping leg and the holding arms accordingly protrude outwardly from the first clamping leg. In a further embodiment which is not shown, the first holding arm is arranged on the first clamping leg and the second holding arm is arranged on the second clamping leg, wherein the holding arms each protrude laterally from the clamping legs.

Since the two holding arms 7, 8 protrude outwardly from the second clamping leg 5, the holding clip 3 also functions as a type of handling aid for the device 1. For example, for factory mounting of the device 1 on the medical hose line, the device 1 may be ergonomically held between the thumb and fingers of one hand in the region of the holding clip 3.

In the embodiment in FIGS. 1 and 2, the holding arms 7, 8 and the clamping legs 4, 5 are arranged matched to one another such that the longitudinal axis L1 of the passage 6 and the longitudinal axis L2 of the recess 9 are oriented at least substantially parallel (FIG. 2). In an embodiment which is not shown, the holding clip 3 is instead rotated by 90° relative to its orientation shown in FIGS. 1 and 2, so that the longitudinal axis L1 and the longitudinal axis L2 are oriented orthogonally to one another. Also, further embodiments are conceivable in which the holding clip 3 is rotated by less than or more than said 90°.

In the embodiment shown, the two holding arms 7, 8—at least in the open position—form a hopper-like widened inlet 11. The inlet 11 at one end opens in the radial direction of the passage 6 into an environment which is not designated specifically. At the other end, the inlet 11 opens into the slot 10. The hopper-like widened inlet 11 facilitates a radial insertion of the second hose portion. The inlet 11 extends from top to bottom, relative to the spatial orientation shown in FIGS. 1 and 2, and is oriented orthogonally to the longitudinal axis L2 of the recess 9. The same applies accordingly for the slot 10. In any case in the open position, the inlet has an inner width, oriented transversely to its longitudinal extent, which is greater than an inner width of the slot 10.

In the embodiment shown, the holding arms 7, 8 are elongate and have a slender cross-section relative to their longitudinal extent. The first holding arm 7 extends between a proximal end 71 and a distal end 72. The second holding arm 8 extends between a proximal end 81 and a distal end 82. The proximal ends 71, 81 of the holding arms 7, 8 are in this case each assigned to the hose clamp 2, more precisely its second clamping leg 5, and fixedly connected thereto. The distal ends 72, 82 of the holding arms 7, 8 however face away from the hose clamp 2. In the present case, the two holding arms 7, each have an S-shape S. Also, the two holding arms 7, 8 are arranged mirror-symmetrically relative to a plane of symmetry (not designated specifically), wherein said plane of symmetry in the present case is a vertical central longitudinal plane of the holding clip 3 and/or the device 1.

The first holding arm 7 has a first curved portion 73 and a second curved portion 74. The first curved portion has a concave curvature relative to the radial direction of the recess 9. The second curved portion 74 however has a convex curvature. The same applies accordingly to the second holding arm 8, so that this too has correspondingly curved first and second curved portions 83, 84. The first curved portion 73 comprises, at its end facing the hose clamp 2, the proximal end 71 of the first holding arm 7. At the other end, the first curved portion 73 transforms into the second curved portion 74. The second curved portion 74 comprises, at its end facing away from the hose clamp 2, the distal end 72 of the first holding arm 7. The same applies accordingly to the first curved portion 83 and second curved portion 84 of the second holding arm 8.

The passage 6 is bordered by the two first curved portions 73, 83. The slot 10 and the inlet 11 are bordered by the second curved portions 74, 84.

In the present case, both the first holding arm 7 and the second holding arm 8 each have an approximately square cross-section. In an embodiment which is not shown, instead a round, in particular circular cross-section of the holding arms is provided.

In the embodiment in FIGS. 1 and 2, the hose clamp 2 and the holding clip 3 are integrally cohesive. Accordingly, the hose clamp 2 and the holding clip 3 form a common component B. The competent B is made of a plastic which is not designated specifically. Preferably, it is produced by injection moulding.

To allow simple production, the first holding arm 7 and the second holding arm 8 in the present case are arranged offset to one another by a longitudinal offset V along the longitudinal axis L2. This is particularly clear from FIG. 2. Because of the longitudinal offset V, the first holding arm 7 and the second holding arm 8 do not lie precisely congruently opposite each other, but instead are offset to one another by said longitudinal offset V in the axial direction of the recess 9. The longitudinal offset V is dimensioned such that mutually opposite inner sides (not designated specifically) of the first holding arm 7 and second holding arm 8 are spaced apart from one another by a gap G along the longitudinal axis L2. The longitudinal offset V and/or the gap G allows use of comparatively simple injection moulding tools, so that the component B can be produced as easily and hence economically as possible. In an embodiment which is not shown in the drawings, the holding arms are oriented with opposite longitudinal slopes, wherein the opposite longitudinal slopes also create a gap for easier removal of the component B from the mould. Such a longitudinal offset and/or opposite longitudinal slope may also be provided in portions of the hose clamp. This further simplifies production. In a further embodiment which is not shown in the drawings, leg portions of the clamping legs, arranged for example in the transverse direction on both sides of the passage, have a longitudinal offset along the longitudinal axis of the passage and/or opposite longitudinal slopes.

In the embodiment shown, the holding arms 7, 8 are each spring-elastically flexible for movement between the holding position and the open position (FIGS. 1, 2). The spring-elastic flexibility and/or bendability is achieved firstly by the slender form of the holding arms 7, 8. Secondly, it is achieved by a corresponding choice of material, wherein in the present case plastic is selected as the material. The spring-elastic flexibility of the holding arms 7, 8 also allows a movement beyond the open position (FIGS. 1, 2), in which the holding arms 7, 8 are moved further away from one another for wider opening of the slot 10 and hence also of the inlet 11. In an embodiment which is not shown in the drawings, the holding arms 7, 8 are instead movable as rigid bodies between the holding and open positions. To this end, in the region of their respective proximal end, the holding arms may be pivotably movable relative to one another about a pivot axis in the geometric and/or spatial-physical sense.

For insertion of the second hose portion which is to be held between the holding arms 7, 8, this is moved in the radial direction of the recess 9, starting from the environment, through the hopper-like inlet 11, into the slot 10 and then from there into the recess 9. Depending on the diameter of the second hose portion, here the holding arms 7, 8 may in some cases be bent away from one another in spring-elastic fashion. This applies in any case if an outer diameter of the second hose portion is greater than the inner width of the slot 10. As soon as the second hose portion has been introduced into the recess 9 in the above-described fashion, the holding arms 7, 8 may be moved from the open position into the holding position.

In the embodiment shown, the holding arms 7, 8 in the holding position are arranged crossed over one another and hooked together in the region of their respective distal ends 72, 82 and/or second curved portions 74, 84. The slot 10 is completely closed by this crossing and engagement of the holding arms 7, 8, countering any radial slippage of the second hose portion out of the recess 9. For engagement, the first holding arm 7 is bent in the direction of the second holding arm 8, and vice versa. Also, in the crossed and/or bent state of the holding arms 7, 8, the distal ends 72, 82 move past one another along the longitudinal axis L2, so that the holding arms 7, 8 are finally hooked together. To hinder an undesired release of the engagement, the holding arms 7, 8 each have a thickening 75, 85 at their distal end faces. In the embodiment shown, the thickenings 75, 85 are each formed as a ball. The ball-shaped thickenings 75, 85 prevent an undesired sliding of the holding arms 7, 8 on one another out of the crossed and engaged configuration. Insofar as a crossing and engagement of the holding arms is provided, as in the embodiment shown, the second curved portions may also be described as hook portions.

In the embodiment in FIGS. 1 and 2, the inner width of the passage in the release position, i.e. the first inner width W1, corresponds approximately to an outer diameter of the first hose portion to be clamped. In other words, dimensionally, the passage 6 is configured to receive and clamp a (single) first hose portion. However, dimensionally, the recess 9 is configured to receive multiple second hose portions to be held. Accordingly, the recess 9 has a diameter D which is many times greater the first inner width W1 of the passage 6 in the release position. In other words, several second hose portions may be held in the recess 9. Accordingly, the cross-sectional area of the recess 9 associated with the diameter D is many times greater the cross-sectional area of the second hose portion.

In the embodiment shown, the clamping legs 4, 5 of the hose clamp are each spring-elastically flexible for movement between the clamping and the release position. To this end, the clamping legs 4, 5 are connected together at one end, forming a solid-state hinge F. The solid-state hinge F allows said spring-elastic flexibility of the clamping legs 4, 5. A hinge axis (not designated specifically) of the solid-state hinge F is oriented approximately horizontally and orthogonally to the longitudinal axis L1 of the passage 6. In an embodiment which is not shown in the drawings, instead a movability of the clamping legs as rigid bodies between the clamping and the release position may be provided. To this end, the clamping legs may be pivotable relative to one another about a pivot axis in the geometric and/or spatial-physical sense.

The solid-state joint F is formed at one end of the two clamping legs 4, 5. At the other end, the clamping legs 4, 5 each have on their end face a latching portion 41, 51, which may be described as the first latching portion 41 and second latching portion 51. In the clamping position, the first latching portion 41 of the first clamping leg 4 and the second latching portion 51 of the second clamping leg 5 are releasably latched together. This counters an undesired release of the hose clamp 2 from the clamped position.

The passage 6 is arranged approximately centrally relative to a main extent direction of the hose clamp 2 oriented along the longitudinal axis L1. In particular, the passage 6 is formed between clamping edges 42, 52 of the clamping legs 4, 5. The clamping edges 42, 52 may also be described as the first clamping edge 42 and second clamping edge 52. The clamping edges 42, 52 are arranged on mutually opposing sides of the passage 6 and border the latter.

In the embodiment shown, the passage 6 may be regarded as a portion of a channel K extending through the hose clamp 2 along the longitudinal axis L1. The channel K extends between a first opening 21, arranged in the region of the solid-state hinge F, and a second opening 22 opposite this along the longitudinal axis L1. Irrespective of whether the clamping position or the release position is assumed, the passage 6 forms a constriction point of the channel K. During use of the device 1, the medical hose line to be clamped—more precisely, the first hose portion—enters the channel K of the hose clamp 2 at one end through the first opening 21. At the other end, the first hose portion emerges from the channel K through the second opening 22. The openings 21, 22 are bordered all round, so that the medical hose line is held radially captive at the hose clamp 2, and vice versa.

Figure 3:
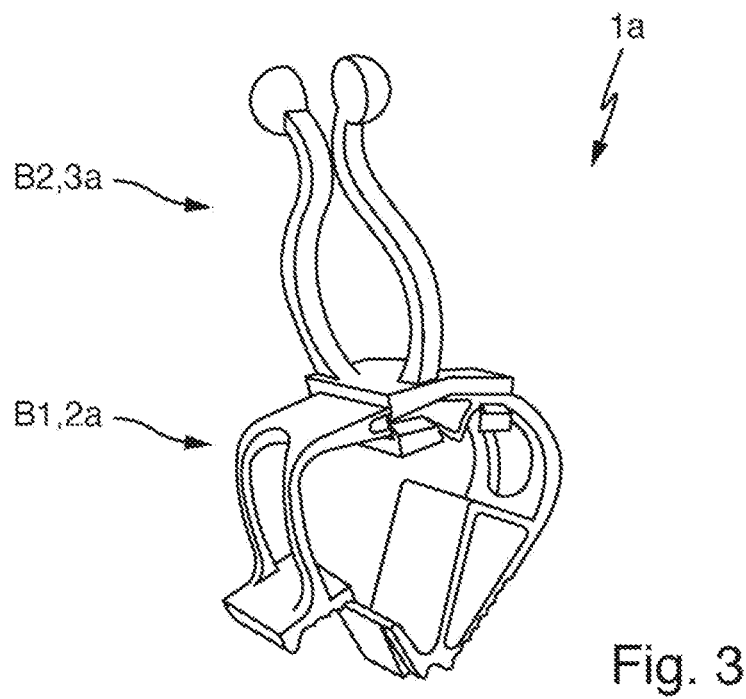
FIG. 3 shows, in a schematic perspective illustration, a further embodiment of a device according to the present disclosure.

With reference to FIG. 3, a further embodiment of a device 1a according to the present disclosure is shown. The device 1a is largely identical to the device 1 in FIGS. 1 and 2. To avoid repetition, only substantial differences between the device 1a and the device 1 are explained below.

The device 1a again comprises a hose clamp 2a and a holding clip 3a. The essential difference of the device 1a from the device 1 is that the hose clamp 2a and the holding clip 3a each form an integral component, so that the entire device 1a is formed in two pieces, in contrast to the device 1 in FIGS. 1 and 2. The hose clamp 2a accordingly forms a first component B1. The holding clip 3a forms a second component B2. The first component B1 and the second component B2 are joined together. In the present case, a releasable joint connection (to be described in more detail) is formed between the first component B1 and the second component B2. Otherwise, the hose clamp 2a is designed identically to the hose clamp 2.

The same applies accordingly with respect to the holding clip 3a. To this extent, no further explanations are necessary concerning the function and design of the clamping legs and/or holding arms of the device 1a. Instead, reference is expressly made to the statements already made with respect to the device 1.

Figure 4:
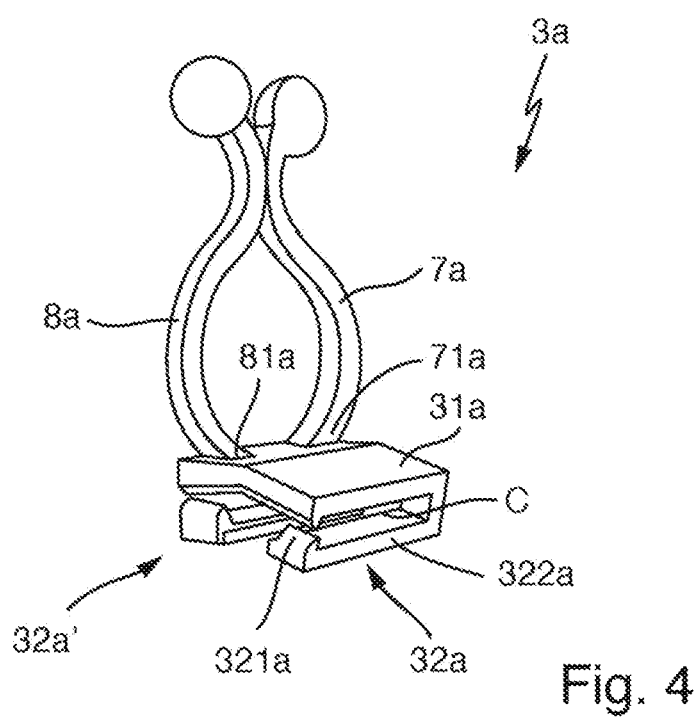
FIG. 4 shows, in a perspective detail illustration, a holding clip of the device from FIG. 3.

FIG. 4 shows the holding clip 3a of the device 1a from FIG. 3 in detail. The holding clip 3a has a foot portion 31a from which the holding arms 7a, 8a protrude. Their proximal ends 71a, 81a transform integrally into the foot portion 31a. For fixing to the hose clamp 2a, the holding clip 3a has at least one latching portion 32a, wherein in the present case two latching portions 32a, 32a' are provided. These are structured identically, so to avoid repetition, only the latching portion 32a will be described in detail below. This has a spring element 322a and a latching geometry 321a in the form of a latching hook arranged on the end face of the spring element 322a. The spring element 322a is configured in the form of a bending bar. The latching portion 32a is arranged on the underside of the foot portion 31a and spaced apart therefrom by a receiving slot C. The receiving slot C is dimensionally matched to a wall thickness of the second clamping leg of the hose clamp 2a. In the joined state shown in FIG. 3, the foot portion 31a is pushed laterally onto the hose clamp 2a, more precisely onto its second clamping leg, and latches with its outer contour.

Figure 5:
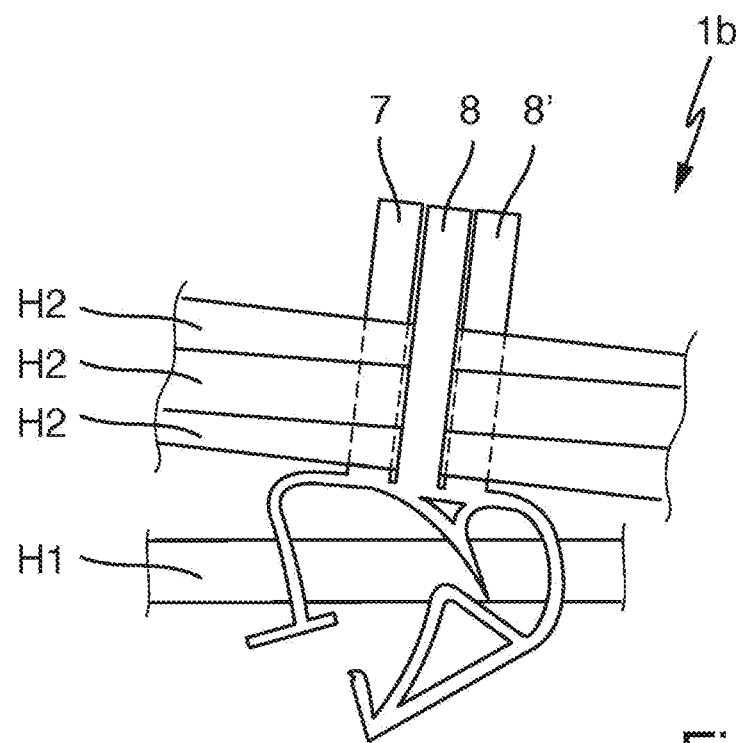
FIG. 5 shows, in a schematic side view, a further embodiment of a device according to the present disclosure, together with several hose portions of a medical hose line.

FIG. 5 shows a further embodiment of a device 1b according to the present disclosure. The device 1b is largely identical to the device 1 from FIGS. 1 and 2. To avoid repetition, only substantial differences are discussed. Otherwise, the statements already made with respect to the device 1 also apply to the device 1*b* from FIG. 5.

The essential difference of the device 1*b* from the device 1 is that an additional holding arm 8' is provided, which may also be described as a third holding arm 8'. The third holding arm 8' is again arranged longitudinally offset to the second holding arm 8 (see FIG. 2). The third holding arm 8' is designed and oriented identically to the first holding arm 7, apart from its longitudinal offset.

Also, FIG. 5 shows the first hose portion H1 and at least one second hose portions H2, more precisely three second hose portions H2. The first hose portion H1 and the second hose portions H2 may be mutually connected portions of the same medical hose line, or separate portions of different medical hose lines.

The invention claimed is:

1. A device for clamping and holding medical hose lines, the device comprising:
    a medical hose clamp with a first clamping leg and a second clamping leg, the first and second clamping legs arranged on opposite sides of a channel, wherein the channel is configured to receive a first hose portion to be clamped between the first and second clamping legs, and wherein the first and second clamping legs are movable relative to one another between a clamping position, in which the first and second clamping legs are moved towards one another in order to constrict the channel and clamp the first hose portion, and a release position in which the constriction is eliminated; and
    a holding clip connected to the medical hose clamp and having at least two holding arms which are arranged opposite one another bordering a recess, wherein the recess is configured to receive at least one second hose portion to be held between the at least two holding arms, and wherein the at least two holding arms are movable relative to one another between an open position, in which the at least two holding arms are moved away from one another and expose a slot that opens radially into the recess, and a holding position in which the slot is closed or at least constricted,
    the first clamping leg defining a first opening enclosed within the first clamping leg,
    the second clamping leg defining a second opening enclosed within the second clamping leg,
    the first opening defining a first end of the channel and the second opening defining a second end of the channel, with the channel defining a longitudinal axis that extends through the first opening and the second opening,
    the first opening and the second opening being configured to align and longitudinally receive the first hose portion, so that the first hose portion extends longitudinally through the channel, with the first clamping leg enclosing a first circumference of the first hose portion, and the second clamping leg enclosing a second circumference of the first hose portion,
    the medical hose clamp further comprising a first clamping edge and a second clamping edge, the first and second clamping edges positioned on opposite sides of the channel and extending transversely to the longitudinal axis,
    the first and second clamping edges facing inwardly toward the longitudinal axis and defining a passage between the first and second clamping edges, with the passage defining a constriction point in the channel where the first hose portion is clamped when the first and second clamping legs are in the clamping position,
    wherein the recess is configured to receive several second hose portions to be held and has a diameter which is greater than an inner width of the passage in the release position.

2. The device according to claim 1, wherein the holding clip is arranged on the first clamping leg and the at least two holding arms each protrude from the first clamping leg.

3. The device according to claim 1, wherein the at least two holding arms and the first and second clamping legs are arranged such that a longitudinal axis of the recess and the longitudinal axis of the channel are oriented parallel.

4. The device according to claim 3, wherein the at least two holding arms are arranged offset to one another by a longitudinal offset along the longitudinal axis of the recess.

5. The device according to claim 1, wherein the at least two holding arms, at least in the open position, form a hopper-like widened inlet which, in a radial direction of the recess, opens at a first end into an environment and opens at a second end into the slot.

6. The device according to claim 1, wherein each holding arm has an S-shape and is arranged mirror-symmetrically with respect to a plane of symmetry.

7. The device according to claim 1, wherein for movement between the holding position and the open position, the at least two holding arms are spring-elastically flexible and/or elastically preloaded in a direction of the holding position.

8. The device according to claim 1, wherein the at least two holding arms, in the holding position, are arranged crossed over one another and hooked together in a region of a respective end facing away from the medical hose clamp.

9. The device according to claim 1, wherein the at least two holding arms comprise three holding arms.

10. The device according to claim 1, wherein for movement between the clamping position and the release position, the first and second clamping legs are each spring-elastically flexible and/or elastically preloaded in a direction of the release position.

11. The device according to claim 1, wherein the first and second clamping legs each have an end face with a latching portion, wherein the latching portions are releasably latched together in the clamping position.

12. The device according to claim 11, wherein the holding clip has a foot portion from which the at least two holding arms protrude, and the foot portion comprises at least one latch arranged on the foot portion, the latch being configured for latching to an outer contour of the medical hose clamp.

13. The device according to claim 1, wherein the medical hose clamp and the holding clip are integrally cohesive and form a common component.

14. The device according to claim 1, wherein the medical hose clamp forms an integral first component, the holding clip forms an integral second component, and the integral first component and the integral second component are joined together.

15. A medical hose line set comprising:
    a medical hose line having a coiled portion comprising a plurality of windings;
    a medical hose clamp comprising a first clamping leg and a second clamping leg; and
    a holding clip connected to the hose clamp and having at least two holding arms which are arranged opposite one another bordering a recess,
    the at least two holding arms enclosing the plurality of windings in the recess to retain the plurality of windings in a coil;
    the at least two holding arms being movable relative to one another between an open position, in which the at least two holding arms are moved away from one another and expose a slot that opens radially into the recess, and a holding position in which the slot is closed or at least constricted, the first clamping leg defining a first opening and the second clamping leg defining a second opening, the first opening defining a first end of a channel and the second opening defining a second end of the channel, with the channel defining a longitudinal axis that extends through the first opening and the second opening, the first opening and the second opening configured to receive an uncoiled portion of the medical hose line that extends from the coiled portion, and hold the uncoiled portion adjacent to the coiled portion, the medical hose clamp further comprising a first clamping edge and a second clamping edge, the first and second clamping edges positioned on opposite sides of the channel and extending transversely to the longitudinal axis, the first and second clamping edges facing inwardly toward the longitudinal axis and defining a passage between the first and second clamping edges, with the passage defining a constriction point in the channel configured to clamp the uncoiled portion when the uncoiled portion is received in the channel, the first and second clamping legs being movable relative to one another between a clamping position, in which the first and second clamping edges constrict the passage to clamp the uncoiled portion, and a release position in which the constriction is eliminated and the uncoiled portion is unclamped, wherein the recess has a diameter which is greater than an inner width of the passage in the release position.

\* \* \* \* \*

UNITED STATES PATENT AND TRADEMARK OFFICE
CERTIFICATE OF CORRECTION

PATENT NO. : 11,957,865 B2
APPLICATION NO. : 17/863375
DATED : April 16, 2024
INVENTOR(S) : Kai-Uwe Ritter Page 1 of 1

It is certified that error appears in the above-identified patent and that said Letters Patent is hereby corrected as shown below:

On the Title Page

Amend to include the following foreign priority data:
Foreign Application Priority Data
Jul. 14, 2021 (DE) .......................... 10 2021 207 509.6

Signed and Sealed this
Twenty-fourth Day of September, 2024

Katherine Kelly Vidal
*Director of the United States Patent and Trademark Office*